(12) United States Patent
Baxter et al.

(10) Patent No.: US 10,258,490 B2
(45) Date of Patent: Apr. 16, 2019

(54) SPLIT SHEATH PROSTHESIS DEPLOYMENT SYSTEM WITH DIVIDED TIP

(71) Applicant: COOK MEDICAL TECHNOLOGIES LLC, Bloomington, IN (US)

(72) Inventors: Charles L. Baxter, West Lafayette, IN (US); Ryan C. Bradway, Tacoma, WA (US)

(73) Assignee: Cook Medical Technologies LLC, Bloomington, IN (US)

( * ) Notice: Subject to any disclaimer, the term of this patent is extended or adjusted under 35 U.S.C. 154(b) by 240 days.

(21) Appl. No.: 15/251,918

(22) Filed: Aug. 30, 2016

(65) Prior Publication Data

US 2017/0056225 A1 Mar. 2, 2017

Related U.S. Application Data

(60) Provisional application No. 62/212,767, filed on Sep. 1, 2015.

(51) Int. Cl.
*A61F 2/97* (2013.01)
*A61F 2/966* (2013.01)
(Continued)

(52) U.S. Cl.
CPC .............. *A61F 2/966* (2013.01); *A61F 2/07* (2013.01); *A61F 2/954* (2013.01); *A61F 2/958* (2013.01);
(Continued)

(58) Field of Classification Search
CPC .. A61F 2/966; A61F 2/07; A61F 2/954; A61F 2/958; A61F 2/962; A61F 2/97
See application file for complete search history.

(56) References Cited

U.S. PATENT DOCUMENTS

2003/0191516 A1 10/2003 Weldon et al.
2004/0127912 A1* 7/2004 Rabkin ..................... A61F 2/95
606/108

(Continued)

FOREIGN PATENT DOCUMENTS

EP 0696447 A2 2/1996
EP 0990426 A1 4/2000
(Continued)

OTHER PUBLICATIONS

Extended European Search Report for EP Application No. 16275123, dated Oct. 27, 2016, 7 pages.
(Continued)

*Primary Examiner* — Tuan V Nguyen
(74) *Attorney, Agent, or Firm* — Brinks Gilson & Lione (57) ABSTRACT

A prosthesis delivery device includes an inner cannula, a positioner disposed coaxially over a first portion of the inner cannula, a concentric cannula disposed coaxially over a second portion of the inner cannula, and a tip assembly disposed over a third portion of the inner cannula. A distal end of the concentric cannula is attached to a proximal end of the positioner. The tip assembly comprises a distal tip segment and a proximal tip segment, with the distal tip segment attached to a proximal end of the concentric cannula and the proximal tip segment attached to a proximal end of the inner cannula. A prosthesis is carried on the concentric cannula and a sheath is mounted coaxially over the prosthesis. The sheath comprises a split defining a proximal sheath segment and a distal sheath segment. A proximal end of the proximal sheath segment is attached to the proximal tip segment.

13 Claims, 6 Drawing Sheets

(51) Int. Cl.
*A61F 2/954* (2013.01)
*A61F 2/962* (2013.01)
*A61F 2/07* (2013.01)
*A61F 2/958* (2013.01)
*A61F 2/95* (2013.01)

(52) U.S. Cl.
CPC ............... *A61F 2/962* (2013.01); *A61F 2/97* (2013.01); *A61F 2002/9511* (2013.01); *A61F 2002/9517* (2013.01); *A61F 2002/9522* (2013.01); *A61F 2002/9665* (2013.01); *A61F 2220/005* (2013.01); *A61F 2220/0058* (2013.01); *A61F 2250/006* (2013.01); *A61F 2250/0069* (2013.01); *A61F 2250/0098* (2013.01); *A61F 2310/00017* (2013.01); *A61F 2310/00023* (2013.01)

(56) References Cited

U.S. PATENT DOCUMENTS

| | | |
|---|---|---|
| 2004/0138734 A1 | 7/2004 | Chobotov et al. |
| 2007/0250069 A1 | 10/2007 | Carlson et al. |
| 2011/0270372 A1 | 11/2011 | Argentine |
| 2011/0307049 A1 | 12/2011 | Kao |
| 2013/0190859 A1* | 7/2013 | Hillukka ............... A61F 2/2427 623/2.11 |

FOREIGN PATENT DOCUMENTS

| | | |
|---|---|---|
| EP | 2522315 A1 | 11/2012 |
| EP | 2907485 A1 | 8/2015 |
| GB | 2474252 A | 4/2011 |
| GB | 2491478 A | 12/2012 |
| WO | WO 98/53761 A1 | 12/1998 |
| WO | WO 03/068302 A2 | 8/2003 |
| WO | WO 2006/037086 A1 | 4/2006 |
| WO | WO 2008/066923 A1 | 6/2008 |
| WO | WO 2011/049808 A1 | 4/2011 |
| WO | WO 2011/059707 A1 | 5/2011 |

OTHER PUBLICATIONS

Extended European Search Report for EP Application No. 16275124, dated Oct. 27, 2016, 5 pages.
Partial European Search Report for EP Application No. 16275125, dated Oct. 27, 2016, 6 pages.
Extended European Search Report for EP Application No. 16275125, dated Nov. 28, 2016, 11 pages.
Extended European Search Report for EP Application No. 16275126, dated Oct. 27, 2016, 7 pages.
Extended European Search Report for EP Application No. 16275127, dated Oct. 27, 2016, 6 pages.

* cited by examiner

SPLIT SHEATH PROSTHESIS DEPLOYMENT SYSTEM WITH DIVIDED TIP

RELATED APPLICATIONS

The present patent document claims the benefit of the filing date under 35 U.S.C. § 119(e) of Provisional U.S. Patent Application Ser. No. 62/212,767, filed Sep. 1, 2015, and entitled PROSTHESIS DELIVERY DEVICE, which is hereby incorporated by reference.

BACKGROUND

The present disclosure relates generally to medical devices, and more particularly, to a system and methods for placement and deployment of a prosthesis in a vessel lumen.

The use of delivery devices or introducers employing catheters has long been known for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, it has also long been known to deliver an implantable medical device by means of a catheter, often intraluminally. For example, a stent, stent-graft, vena cava filter or occlusion device may be delivered intraluminally from the femoral artery, via a transapical approach and/or using other acceptable delivery locations and methods for deployment of the prosthesis.

For procedures in which a prosthesis or other medical device is implanted into a patient, the prosthesis to be implanted is normally held on a carrier catheter or cannula of the introducer in a compressed state and then released from the cannula so as to expand to its normal operating state, prior to withdrawal of the cannula from the patient to leave the implant in position. In many devices, the steps to carry out the implantation may occur, for example, first by retracting a retractable sheath to expand or partially expand the prosthesis, and then performing further steps to, for example, release one or both ends of the prosthesis, deploy an anchoring stent, or the like.

The prosthesis which is to be implanted within a patient's vasculature by the delivery device may vary depending on various factors including the procedure being performed and the portion of the vasculature being treated. The delivery device described herein can be configured to deploy a wide range of different prostheses including, but not limited to cuffs, single lumen tubular stent grafts, bifurcated AAA stent grafts, branched or fenestrated stent grafts and combinations thereof. In addition to facilitating the delivery of a wide range of prostheses, the delivery device can be used for a variety of delivery approaches to be utilized, including but not limited to transapical or femoral approaches.

While the embodiments disclosed herein may be generally discussed in relation to a delivery device for a stent graft and method of deployment thereof into one or more specific arteries, including the aorta and iliac arteries, it is also contemplated that the present disclosure is not so limited and may relate to any prosthesis and/or any body or vessel lumen in which such a deployment is necessary or desired.

BRIEF SUMMARY

In one aspect, a system for the delivery and deployment of a prosthesis comprises a delivery device having a distal end and a proximal end. The delivery device comprises an inner cannula extending between the distal end and the proximal end of the delivery device, a positioner disposed coaxially over a first portion of the inner cannula, a concentric cannula disposed coaxially over a second portion of the inner cannula, and a tip assembly disposed over a third portion of the inner cannula. A distal end of the concentric cannula is attached to a proximal end of the positioner. The tip assembly comprises a distal tip segment and a proximal tip segment disposed proximally of the distal tip segment, the distal tip segment being attached to a proximal end of the concentric cannula, the proximal tip segment being attached to a proximal end of the inner cannula. A prosthesis is carried on the concentric cannula at the proximal end of the delivery device and a sheath is mounted coaxially over the prosthesis. The sheath comprises a split defining a proximal sheath segment disposed proximally of the split and a distal sheath segment disposed distally of the split. A proximal end of the proximal sheath segment is attached to the proximal tip segment.

In another aspect, a method of deploying a prosthesis comprises providing a delivery device that includes an inner cannula extending between a distal end and a proximal end of the delivery device, a positioner disposed coaxially over a first portion of the inner cannula, a concentric cannula disposed coaxially over a second portion of the inner cannula, a distal end of the concentric cannula being attached to a proximal end of the positioner, and a tip assembly disposed over a third portion of the inner cannula, the tip assembly having a distal tip segment and a separate proximal tip segment disposed proximally of the distal tip segment, the distal tip segment being attached to a proximal end of the concentric cannula, the proximal tip segment being attached to a proximal end of the inner cannula. The method further comprises providing a prosthesis carried on the concentric cannula at the proximal end of the delivery device and providing a sheath mounted coaxially over the prosthesis, the sheath having a split defining a proximal sheath segment disposed proximally of the split and a distal sheath segment disposed distally of the split, a proximal end of the proximal sheath segment being attached to the proximal tip segment. In addition, the method comprises pushing the proximal sheath segment proximally simultaneously with the proximal tip segment so as to at least partially remove the proximal sheath segment from the prosthesis.

DETAILED DESCRIPTION

In the present disclosure, when referring to a prosthesis delivery device, "proximal" refers to the part of the delivery device that is furthest from the operator of the delivery device and intended for insertion in a patient's body and "distal" refers to that part of the delivery device closest to the operator. With regard to a prosthesis, the term "proximal" refers to that part of the prosthesis that is closest to the proximal end of the delivery device and "distal" refers to the opposite end of the prosthesis. The term "ipsilateral" is used to indicate that the diseased vessel(s) being accessed during a given procedure are on the same side of the body (right or left) as the vascular access delivery device/introducer, while "contralateral" signifies that the vessel(s) of interest are on the opposite side of the body.

Figure 1:
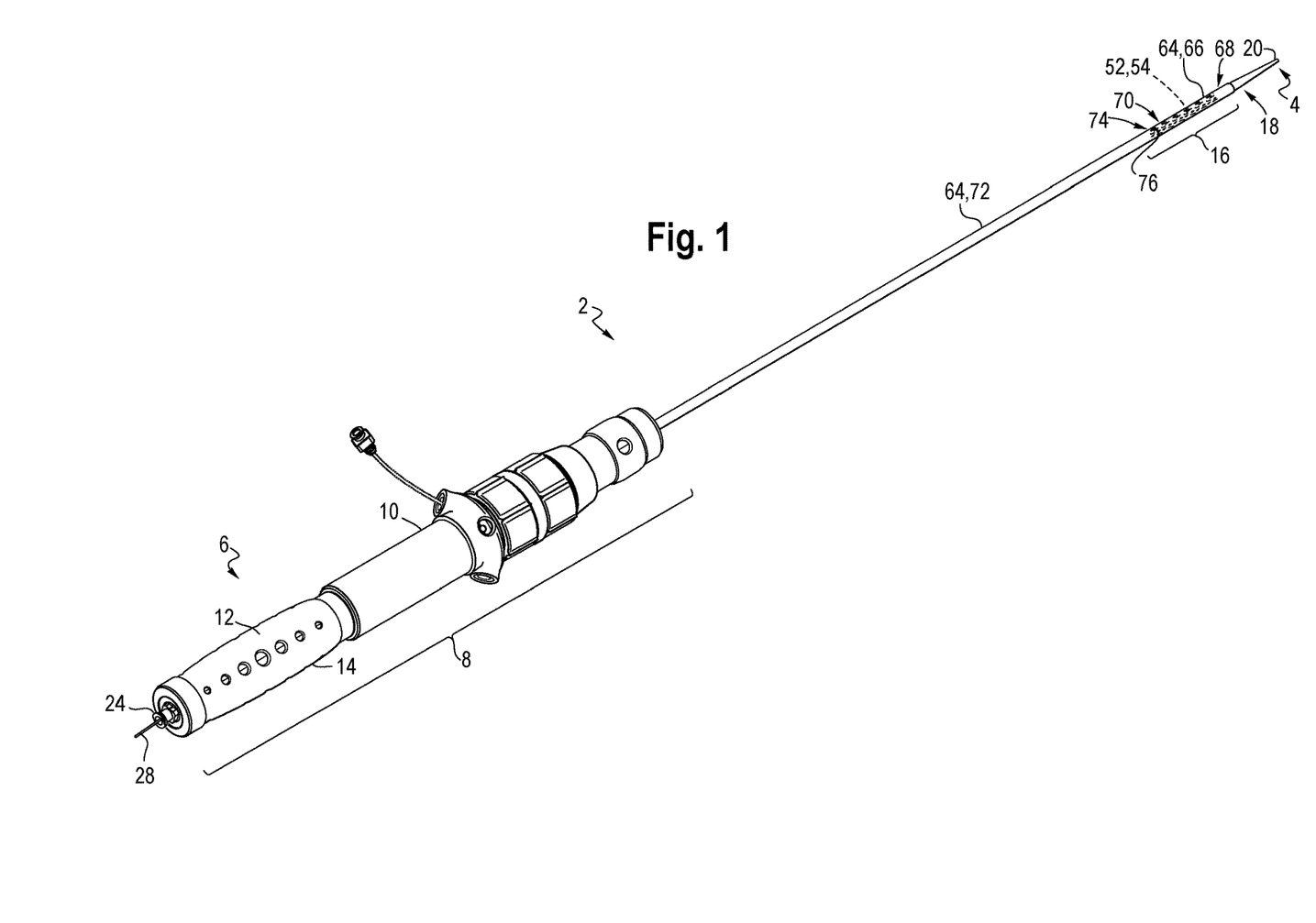
FIG. 1 is a rear perspective view of one example of a delivery device illustrating a split sheath deployment system with a divided tip for placement and deployment of a prosthesis at the proximal end of the delivery device.
Figure 2:
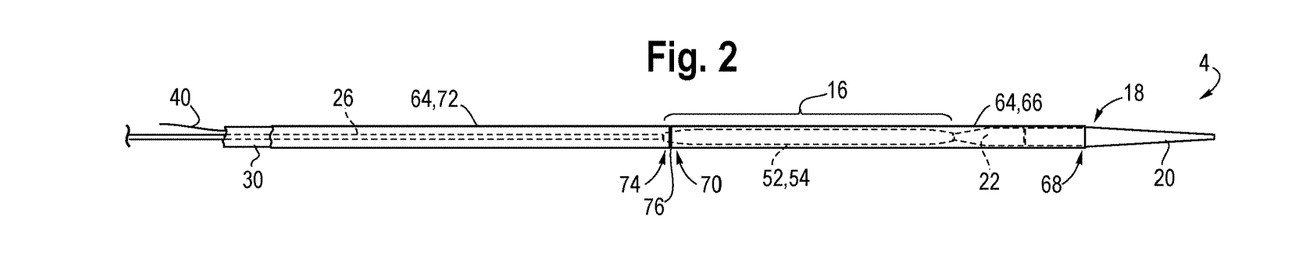
FIG. 2 illustrates the proximal end of the delivery device and the prosthesis fully sheathed.

Referring initially to FIG. 1, an example of a delivery device is shown generally at 2, including a proximal end 4 and a distal end 6. A handle assembly 8 is located adjacent the distal end of the device. A split sheath deployment system with a divided tip can be operated and manipulated using the handle assembly 8, as will be described in further detail below.

In one example, the handle assembly 8 generally includes first or main handle 10, a second or front handle 12 and a third or rear handle 14. The main handle 10 is fixed relative to the delivery device 2. In one example, the main handle 10 may also be fixed relative to the front handle 12 and/or to the rear handle 14, with the front handle 12 and the rear handle 14 being separately and independently rotatable relative to the main handle 10. Further details of examples of a handle assembly that may be used to manipulate the split sheath and divided tip assembly are described herein and in U.S. Provisional Application Nos. 62/064,595 filed on Oct. 16, 2014, which application is incorporated by reference herein in its entirety.

As shown in FIGS. 2-13, the proximal end 4 of the delivery device 2 includes retention region 16 upon which a variety of prostheses 52 can be releasably coupled and a "divided" tip assembly or nose cone dilator 18. The tip assembly 18 includes a proximal tip segment 20 having a forward proximal taper and an inner lumen 20a and a separate distal tip segment 22 having a reverse distal taper and an inner lumen 22a, as shown for example in FIGS. 8-10. The tip assembly 18 presents a smooth tapered surface to facilitate entry into and movement through a body vessel and facilitates deployment of the prostheses 52, as will be described in further detail below. Tip assembly 18 may include radiopaque material or be equipped with a radiopaque marker (not shown) to facilitate visualization of the tip assembly 18 in use provided by desired imaging modality (i.e., by fluoroscopy, MRI, 3D or other imaging techniques).

Figure 3:
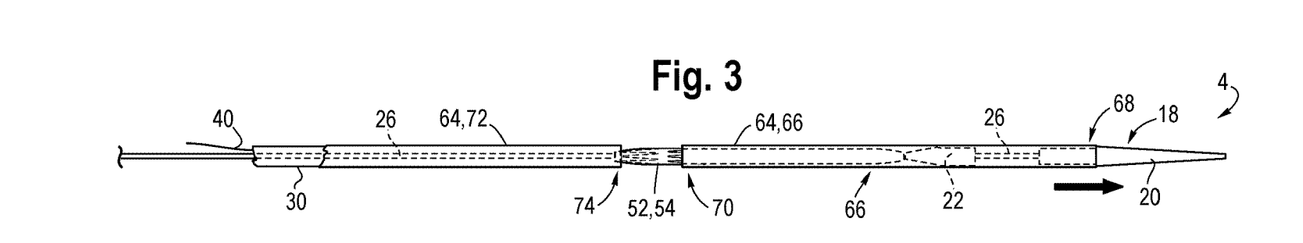
FIG. 3 illustrates the proximal end of the delivery device and the prosthesis partially unsheathed.

An inner cannula 26 extends the longitudinal length of the delivery device 2, from a pin vice 24 at the distal end 6 of the device 2 to the tip assembly 18 at the proximal end 4 of the device 2. The inner cannula 26 may be connected at its distal end within the handle assembly 8 to facilitate pushing the inner cannula forward or proximally relative to the device 2, as described further herein. At its proximal end, the inner cannula 26 is moveably received within the inner lumen 22a of the distal tip segment 22 and is fixedly attached within the inner lumen 20a of the proximal tip segment 20. More particularly, inner cannula 26 extends within the inner lumen 22a of the distal tip segment 22, which may be configured so as to allow inner cannula 26 to move or slide longitudinally therein. Inner cannula 26 also extends within the inner lumen 20a of the proximal tip segment 20, and may be attached or coupled to the proximal tip segment 20 by various means, including adhesives, welding, and/or other suitable attachment mechanism. In one example, inner cannula 26 is attached to the proximal tip segment 20 by an overmolding process and a gluing process. As a result, pushing the inner cannula 26 in a proximal direction simultaneously causes proximal longitudinal movement of the inner cannula 26 as well as proximal movement of the proximal tip segment 20 of the tip assembly 18. Inner cannula 26 has an inner lumen 26a which may accommodate a guide wire 28 for tracking the delivery device 2 to a desired position within a patient's vasculature and which may also be used for flushing or injection of fluids as shown in FIG. 3. The inner cannula 26 may be made of a variety of suitable materials that are stiff, yet flexible enough to allow the inner cannula 26 to conform to the tortious anatomy of a patient during use, and may be either straight or have a curve imparted to a portion of it. For example, the inner cannula 26 may be constructed of polymers, metals and/or alloys, including nitinol or stainless steel.

A stiffening cannula or positioner 30, sometimes also referred to as a pusher, is disposed coaxially over at least a portion of the inner cannula 26. The positioner 30 may be a cannula constructed from various materials, and in one example, a proximal portion of the positioner which is introduced into the patient may comprise a polymer, sometimes referred to as VRDT (or vinyl radiopaque dilator tubing), plastics, metals, alloys or a combination thereof, whereas a distal portion of the positioner 30 may comprise the same material as the proximal portion of the positioner 30 or it may be a different material including but not limited to plastics, polymers, alloys, metals or a combination thereof, that provide sufficient maneuverability and stiffness to the positioner 30 as necessary and desired. The positioner 30 may extend from a location just distal of the prosthesis retention region 16 coaxial with a length of the inner cannula 26 and terminate at a distal end within the handle assembly 8. In one example, the distal end of the positioner 30 may be directly or indirectly attached to the main handle 10 by various means, including threaded attachment, adhesives, welding, and/or other suitable attachment mechanisms. For a length of the positioner 30, a stiffening rod (not shown) may be disposed over the inner cannula 26 and/or over the positioner 30 for additional stability and maneuverability.

A concentric cannula 34 may be disposed coaxially over a portion of the inner cannula 26 at the prosthesis retention region 16. A distal end 36 of the concentric cannula 34 may be attached or coupled to a proximal end 32 of the positioner 30 by various means, including adhesives, welding, and/or other suitable attachment mechanisms. A proximal end 38 of the concentric cannula 34 may be attached or coupled to the distal tip segment 22 of the tip assembly 18 by various means, including adhesives, welding, and/or other suitable attachment mechanisms. The concentric cannula 34 may be constructed from various materials including but not limited to plastics, polymers, alloys, metals or a combination thereof, that provide sufficient maneuverability and stiffness to the concentric cannula 34 as necessary and desired. In one example, concentric cannula 34 may be constructed of a flexible, high-tensile polymeric material such as polyetheretherketone (PEEK).

The delivery device 2 can be used to deliver and deploy a wide variety of prostheses 52, including variously sized and shaped stent grafts. Therefore, FIG. 1 illustrates one exemplary prosthesis 52 in dashed lines to indicate that it is a generic prosthesis for illustrative purposes and that any one or more different prostheses can be interchanged and be releasably coupled to the delivery device 2 in a similar fashion. Several non-limiting examples of prostheses 52, which may be delivered to and deployed within a patient in a controlled and sequential manner using the delivery device 2, are described further herein.

As shown in FIGS. 2-13, the prosthesis 52, such as stent graft 54, is carried on the delivery device 2 at the proximal end 4. More specifically, the prosthesis 52, such as stent graft 54 is carried on the concentric cannula 34 at the prosthesis retention region 16. In one example, a stent graft 54 has an uncoupled state in which the graft is positioned coaxially over the inner cannula 26 and the concentric cannula 34 with the proximal end of the stent graft 54 in longitudinal proximity relative to the distal tip segment 22 of the tip assembly 18. During assembly, the distal end of the stent graft 54 can be releasably coupled to the proximal end 32 of the positioner 30 and the proximal end of the stent graft 54 can be releasably coupled to the distal tip segment 22 of the tip assembly 18, as described below.

The prosthesis 52 may be releasably coupled to the delivery device 2 at the prosthesis retention region 16 in a variety of ways. FIGS. 12-15 illustrate one non-limiting example of an attachment and release mechanism for the distal end of a stent graft 54. In this example, a prosthesis attachment mechanism releasably may couple the distal end 58 of the stent graft 54 to the proximal end 32 of the positioner 30. More particularly, the attachment mechanism may comprise three distal trigger wires 40 each having a proximal end 42. However, other attachment mechanisms, including fewer or more distal trigger wires may also be used to releasably couple the distal end 58 of the stent graft 54 to the positioner 30. Further, other attachment mechanisms, in addition to the one or more distal trigger wires 40, may also be used to couple the distal end 58 of the stent graft 54 to the delivery device 2, such as diameter reducing ties, a retractable sheath, sutures and the like as will be recognized by one of skill in the art. U.S. application Ser. No. 13/970,861 filed on Aug. 20, 2013, describes one example of a releasable diameter reducing tie, which application is incorporated by reference herein in its entirety.

The distal trigger wires 40 may extend longitudinally within a lumen of positioner 30 proximally from the handle assembly 8 to the distal end 58 of the stent graft. More particularly, the distal ends of the distal trigger wires 40 may be coupled to one or more trigger wire release mechanisms that are disposed about and/or around at least a portion of the main handle 10, as described further herein.

The proximal ends 42 of the distal trigger wires 40 exit the positioner 30 at its proximal end 32 and are releasably coupled to the distal end 58 of the stent graft 54. In one example, the distal trigger wires 40 may be directly or indirectly attached to the distal end 58 of the stent graft 54. For example, the distal trigger wires 40 may engage suture loops (not shown) which are attached to the distal end 58 of the stent graft 54. In this way, the trigger wires do not weave directly through the graft material 62. Alternatively, the distal trigger wires 40 may be woven directly through or removably attached to the graft material 62 or woven over or through one or more stents 60 at the distal end 58 of the stent graft 54.

Figures 14, 15, 16, 17:
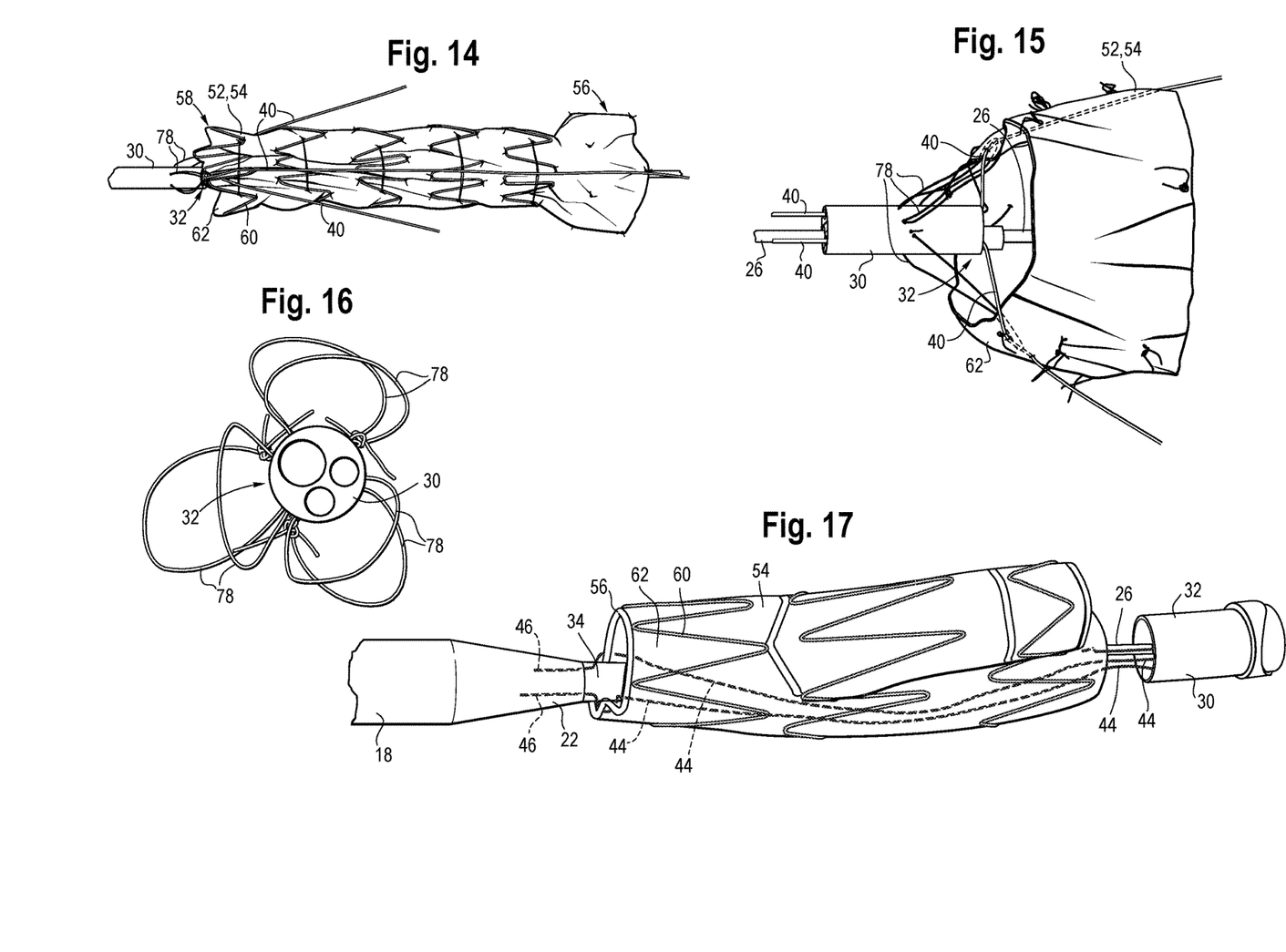
FIG. 14 illustrates an example of an attachment and release mechanism for the distal end of the prosthesis.
FIG. 15 illustrates another example of an attachment and release mechanism for the distal end of the prosthesis.
FIG. 16 is an end view of one example of a positioner with suture loops for the delivery device.
FIG. 17 illustrates an example of an attachment and release mechanism for the proximal end of a prosthesis.

In the example shown in FIGS. 14-16, the three distal trigger wires 40 are woven directly through the graft material 62 at the distal end 58 of the stent graft 54 and engage suture loops 78 attached to the positioner 30 at its proximal end 32. More particularly, the distal trigger wires 40 are woven directly through the graft material 62 at the distal end 58 of the stent graft at three spaced apart points around the periphery of the tubular graft body (for example, at radial positions approximately 120 degrees apart) such that when those points are retained by the trigger wires 40 against the positioner 30, the distal end of the stent graft 54 generally forms a "cloverleaf" formation with each lobe of the "cloverleaf" being approximately the same size. Of course, other points of attachment may also be used to releasably couple the stent graft 54 to the positioner 30 to form various configurations at the distal end 58 of the stent graft 54. After each distal trigger wire 40 penetrates the graft material 62, the wire travels through a suture loop 78 attached to the positioner 30 (for example by tying each suture loop through a hole in the wall of the positioner 30) and then back through the graft material 62. Such a configuration using suture loops 78 attached to the positioner 30 may allow higher deployment and loading forces and than fixation methods using suture loops attached to the stent graft 54 and reduce the risk of structural failure of the positioner, for example, in applications requiring high forces for loading and/or deploying stent grafts 54. This configuration may also prevent undesired rotation of the positioner 30 relative to the stent graft 54 so that the the rotational position of the stent graft 54 can be more accurately adjusted during deployment. In addition, this configuration may reduce the risk of embolization during a procedure in which the stent graft 54 is implanted into a patient by avoiding potentially loose suture loops on the stent graft 54 from being exposed to the blood flow.

Again, stent graft 54 is used for exemplary purposes only in this particular description of proximal stent graft attachment, but any type of prosthesis can be releasably coupled to the inner cannula in this manner. Other suitable attachment methods or mechanisms may be used to removably attach one or more distal trigger wires 40 to the distal end of the stent graft 54, thereby coupling the stent graft to the positioner 30 until the trigger wire(s) are released during deployment, as would be recognized by one of skill in the art. Moreover, the attachment and release mechanism described above may be used to releasably couple a prosthesis to various types of delivery devices, including but not limited to the split sheath deployment system with a divided tip described further herein.

In addition, the delivery device 2 may also include an attachment and release mechanism for the proximal end of the stent graft 54 as described further herein. In one non-limiting example, the proximal attachment mechanism may releasably couple the proximal end 56 of the stent graft 54 to the distal tip segment 22 of the tip assembly 18. More particularly, the proximal attachment mechanism may comprise one or more proximal trigger wires 44 each having a proximal end 46. Other attachment mechanisms, in addition to the one or more proximal trigger wires 44 may also be used to couple the proximal end 56 of the stent graft 54 to the delivery device 2, such as diameter reducing ties, a retractable sheath, sutures and the like as will be recognized by one of skill in the art. U.S. application Ser. No. 13/970,861 filed on Aug. 20, 2013, which application is incorporated by reference herein in its entirety, describes one example of a releasable diameter reducing tie.

In the non-limiting example, the proximal trigger wires 44 may extend longitudinally within a lumen of positioner 30 proximally from the handle assembly 8 and further within a lumen of the stent graft 54 to the proximal end 56 of the stent graft 54. More particularly, the distal ends of the proximal trigger wires 44 may be coupled to one or more trigger wire release mechanisms that are disposed about and/or around at least a portion of the main handle 10, as described further herein. The proximal ends 46 of the one or more trigger wires 44 are releasably coupled to the proximal end 56 of the stent graft 54. In one example, the proximal trigger wires 44 may be directly or indirectly attached to the proximal end 56 of the stent graft 54 to releasably couple the proximal end 56 of the stent graft to the distal tip segment 22 of the tip assembly 18. For example, the proximal trigger wires 44 may engage a suture loop (not shown) which is attached to the proximal end 56 of the stent graft 54. In this way, the trigger wires 44 do not weave directly through the graft material 62. Alternatively, the proximal trigger wires 44 may be woven directly through or removably attached to the graft material 62 or woven over or through one or more stents 60 at the proximal end 56 of the graft 54. In the event that a stent graft 54 includes a bare anchoring stent (not shown) extending proximally from the proximal end 56, the one or more trigger wires my weave over and/or through the proximal bare stent to releasably couple the proximal end 56 of the stent graft to the distal tip segment 22 of the tip assembly 18.

The proximal ends 46 of the one or more proximal trigger wires 44 may be retained within the distal tip segment 22 of the tip assembly 18, such as by friction fit, adhesives, or other suitable releasable attachment means so as to hold the proximal end 56 of the stent graft 54 in a radially inwardly contracted delivery configuration and allow for the trigger wires to be pulled distally and released from the inner cannula 26 when deployment of the proximal end of the stent graft 54 is necessary or desired. Other suitable attachment methods or mechanisms may be used to removably attach the proximal trigger wires 44 to the proximal end of the stent graft 54 as would be recognized by one of skill in the art.

When deployment is desired, distal retraction of the proximal trigger wires 44 and the distal trigger wires 40 (such as by manipulation of one or more trigger wire release mechanisms of the handle assembly 8) allows the proximal ends of the proximal trigger wires 44 and the distal trigger wires 40 to be released from the proximal and distal ends of the stent graft 54, allowing the proximal and distal ends of the stent graft 54 to at least partially deploy radially outwardly within a vessel. If other diameter reducing ties are being used to radially restrain the proximal and distal ends of the stent graft 54, those ties may also be removed by manipulation of the trigger wire release mechanisms to allow the stent graft to move from a radially inwardly constrained delivery configuration to a radially outwardly expanded configuration and fully deploy from delivery device 2 within the vessel.

The above description of the coupling of prosthesis 52 to the delivery device 2 is for exemplary purposes, and shall not be considered limiting, as different prostheses may be releasably coupled to the delivery device in different ways, and the proximal and distal ends of a particular prosthesis may be coupled to the delivery device in different ways. In addition, several other non-limiting examples of attachment and release mechanisms for the distal and proximal ends of the prosthesis 52 that can be operated and manipulated using the handle assembly 8 are described herein.

The releasable coupling of prosthesis 52 to the delivery device 2 at the prosthesis retention region 16 secures the prosthesis 52 to the delivery device 2 to radially inwardly restrain the prosthesis 52 in a manner that may subsequently facilitate insertion of the subassembly comprising the inner cannula 26, the positioner 30, the concentric cannula 34, and the prosthesis 52 into an outer sheath, such as the sheath 64 described below. As will be apparent, the sheath 64 is configured to radially restrain other regions of the prosthesis 52 for delivery in a low-profile configuration to a target site within a patient's anatomy.

As shown in FIGS. 1-2, 8 and 11, the longitudinally slideable and retractable sheath 64 may extend along the length of the delivery device 2 from the front handle 12 to the tip assembly 18. The sheath 64 may be disposed coaxially about and/or over at least a portion of the inner cannula 26. The sheath 64 is configured to cover and assist in retaining a prosthesis 52, such as stent graft, in a radially inwardly compressed, low-profile configuration during delivery of the prosthesis to a target site within a patient's anatomy.

In one example, the sheath 64 may be a "split sheath," meaning that there is a split 76 at a point between the proximal and distal ends of the sheath 64, resulting in a proximal sheath segment 66 and a distal sheath segment 72 that must both be removed to expose the prosthesis 52. The proximal sheath segment 66 may be disposed coaxially over a proximal portion of the inner cannula 26 and may be attached or otherwise secured at its proximal end 68 to the proximal tip segment 20, for example at or about the point where the forward proximal taper of the proximal tip segment begins, such as by adhesives, bonding, welding or other suitable attachment mechanisms. In this way, the proximal sheath segment 66 is indirectly attached to the inner cannula 26 via the proximal tip segment 20. As a result, pushing the inner cannula 26 in a proximal direction simultaneously causes proximal longitudinal movement of the inner cannula as well as proximal movement of the proximal tip segment 20 and the proximal sheath segment 66. The distal sheath segment 72 may be disposed coaxially over at least a portion of the positioner 30 over a distal portion of the inner cannula 26. The distal sheath segment 72 may be connected at its distal end within the handle assembly 8 to facilitate retraction of the distal sheath segment 72 distally, as described further herein.

In one example, the split 76 in the sheath may be generally aligned at the distal end 58 of the prosthesis 52 such that the distal end 70 of the proximal sheath segment 66 and the proximal end 74 of the distal sheath segment 72 are disposed over a portion of the prosthesis 52 at the distal end 58 of the prosthesis. In another example, the split 76 in the sheath may be generally aligned with a fenestration (not shown) in the prosthesis 52, such as stent graft 54. This may allow cannulation of a branch vessel through the fenestration before one or both of the sheath segments are removed.

Before use of the delivery device 2 and during a procedure when the delivery device is tracked to a desired location within a patient's body, the prosthesis 52 at the proximal end 4 of the delivery device 2 is fully covered by sheath 64 and held in a radially inwardly contracted condition. To deploy the prosthesis 52 in a vessel lumen, removal of the proximal sheath segment 66 and the distal sheath segment 72 may proceed in two separate actions or manipulations of the handle assembly 8.

Figure 4:
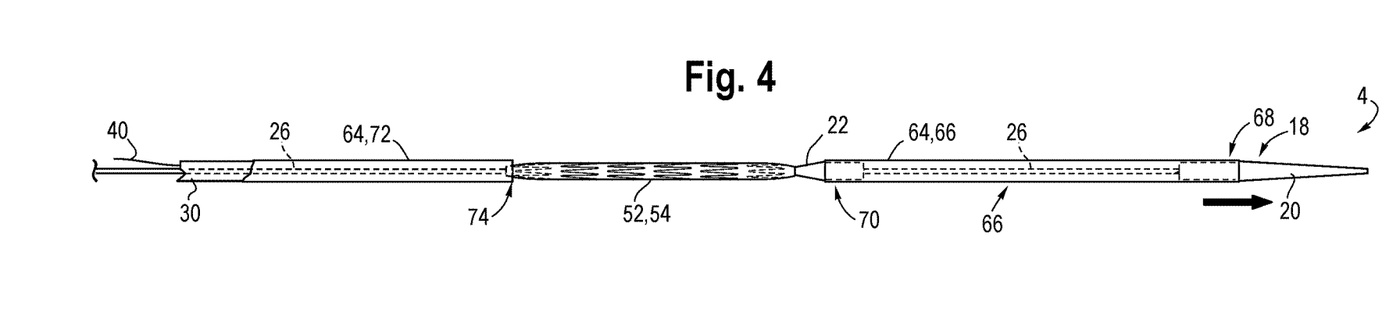
FIG. 4 illustrates the proximal end of the delivery device and the proximal end of the prosthesis fully unsheathed.
Figure 9:
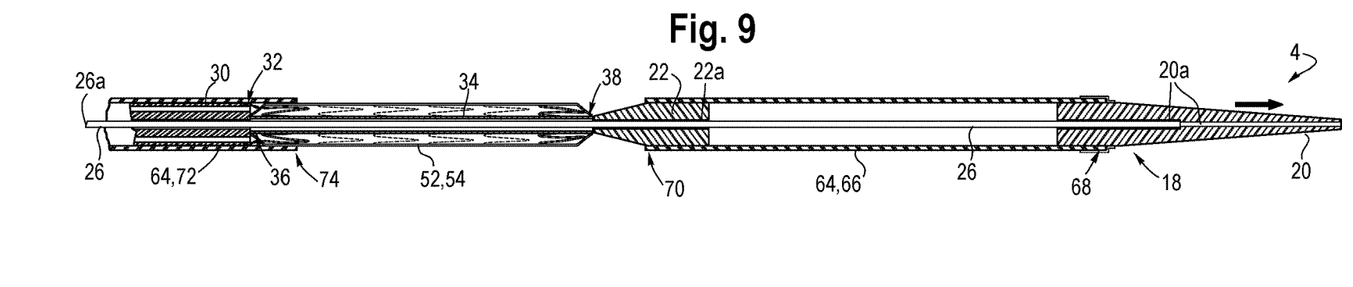
FIG. 9 is a cross-sectional side view of the proximal end of the delivery device and the proximal end of the prosthesis fully unsheathed.

In one example, a first action may be to push the proximal sheath segment 66 of the sheath 64 proximally so as to remove the proximal sheath segment 66 from the prosthesis 52 and expose the proximal end 56 of the prosthesis and the reverse distal taper of distal tip segment 22 of the tip assembly 18 as shown in FIGS. 3, 4 and 9. Several non-limiting examples of using handle 12 to facilitate proximal longitudinal movement of the inner cannula 26, thereby simultaneously pushing the proximal tip segment 20 and the proximal sheath segment 66 proximally, are described further herein. During removal of the proximal sheath segment 66 from the prosthesis 52 over the distal tip segment 22, longitudinal movement of the distal tip segment 22 is prevented because the distal tip segment, being indirectly attached to the positioner 30 and thus the handle 10 via the concentric cannula 34, is held in place.

When the delivery device 2 is used to deliver a prosthesis 52 to a vessel having a branch vessel extending from a main vessel where cannulation of the branch vessel is necessary or desired, the proximal sheath segment 66 may be only partially removed from the prosthesis 52 to expose a fenestration (not shown) in the prosthesis 52 for cannulation of the branch vessel through the fenestration prior to full deployment of the prosthesis 52, as shown in FIG. 3. This may provide a higher degree of control over the position of the prosthesis 52 and delivery device 2 during the cannulation procedure. Once cannulation of the branch vessel is complete, the proximal sheath segment 66 may be pushed further until it is fully removed from the prosthesis 52 and the reverse distal taper of distal tip segment 22 is exposed, as shown in FIGS. 4 and 9. Alternatively, the proximal sheath segment 66 may be fully removed from the prosthesis 52 prior to cannulation.

Figure 5:
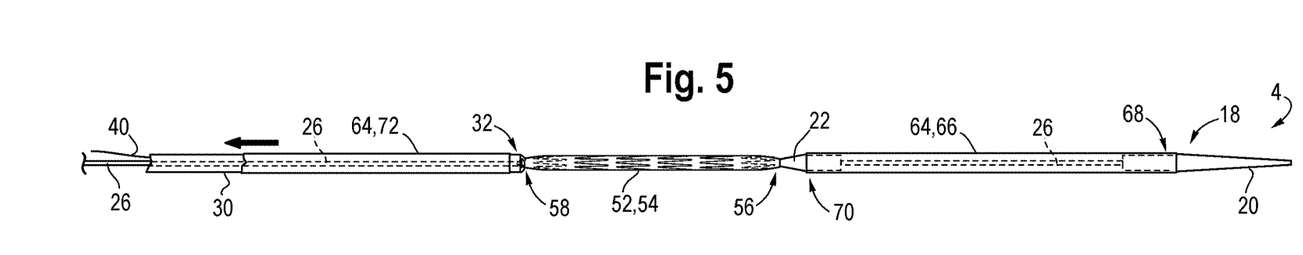
FIG. 5 illustrates the proximal end of the delivery device and the prosthesis fully unsheathed.
Figure 10:
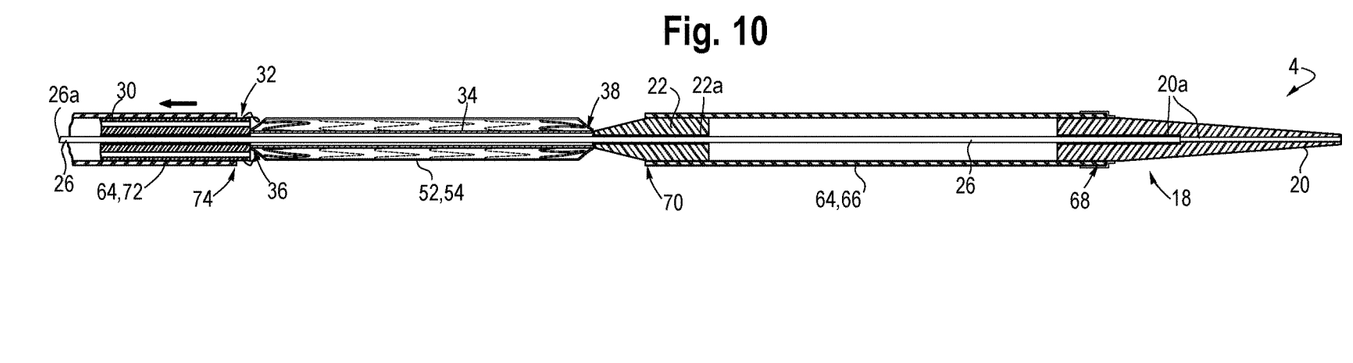
FIG. 10 is a cross-sectional side view of the proximal end of the delivery device and the prosthesis fully unsheathed.
Figures 11, 12, 13:
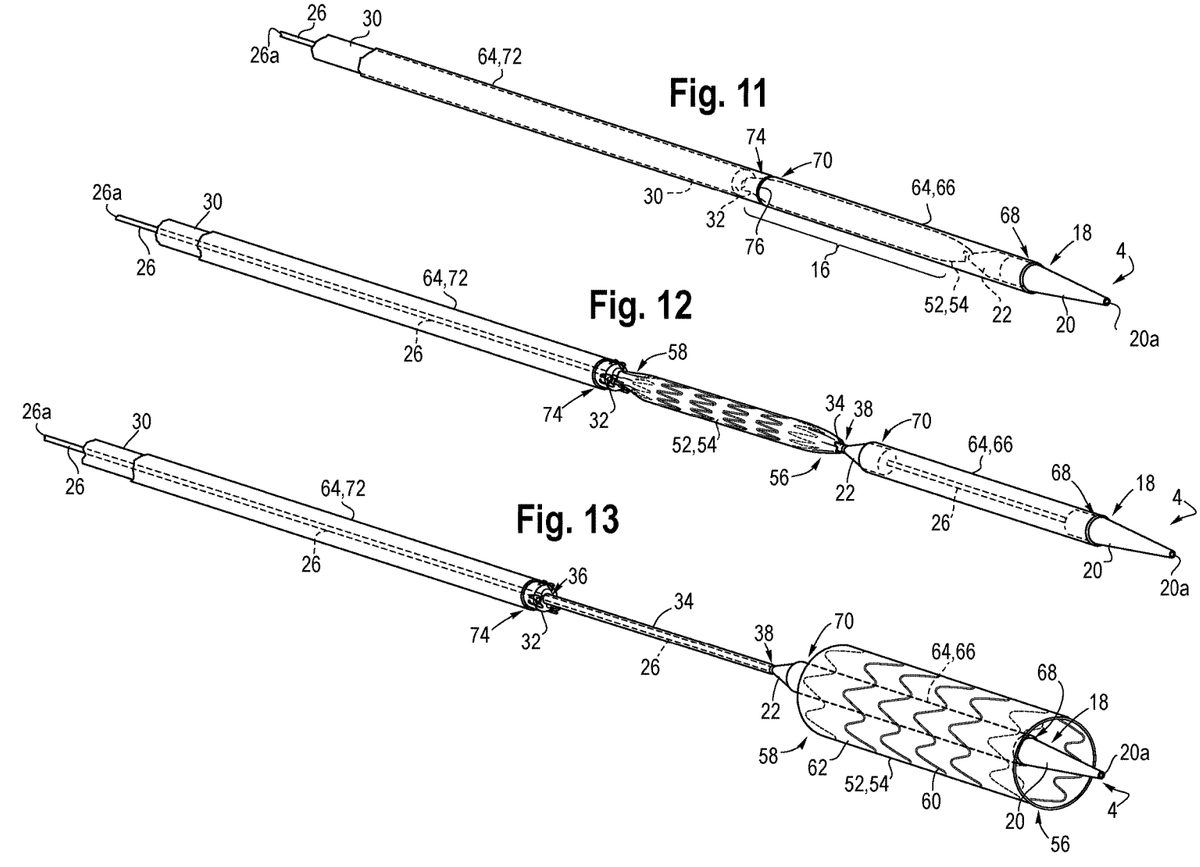
FIG. 11 is a perspective view of the proximal end of the delivery device and the prosthesis fully sheathed.
FIG. 12 is a perspective view of the proximal end of the delivery device and the prosthesis fully unsheathed.
FIG. 13 is a perspective view of the proximal end of the delivery device illustrating the delivery device partially withdrawn after the prosthesis is fully deployed.

The second action may be to retract the distal sheath segment 72 distally over the positioner 30 to remove it from the prosthesis 52 and expose the distal end 58 of the prosthesis at the proximal end 32 of the positioner 30, as shown in FIGS. 5, 10 and 12. Several non-limiting examples of using handle 14 to facilitate retraction of the distal sheath segment 72 so as to remove it from the prosthesis 52, thereby fully exposing the prosthesis 52 between its proximal and distal ends, are described further herein.

In one example, when the proximal sheath segment 66 has been pushed proximally a sufficient distance to expose the proximal end 56 of the prosthesis 52 and before retracting the distal sheath segment 72 distally to expose the distal end 58 of the prosthesis, the user may proceed with removal of at least the proximal trigger wires 44 and any other diameter reducing ties that may be present at the proximal end 56 of the prosthesis (such as by manipulation of one or more trigger wire release mechanisms of the handle assembly 8 to retract the proximal trigger wires 44) to allow the proximal end 56 of the prosthesis to at least partially deploy radially outwardly within a vessel. Alternatively, the user may proceed with removal of at least the proximal trigger wires 44 and any other diameter reducing ties that may be present at the proximal end 56 of the prosthesis after the proximal sheath segment 66 has been pushed proximally a sufficient distance to expose the proximal end 56 of the prosthesis 52 and the distal sheath segment 72 has been retracted distally to expose the distal end 58 of the prosthesis.

Figure 6:
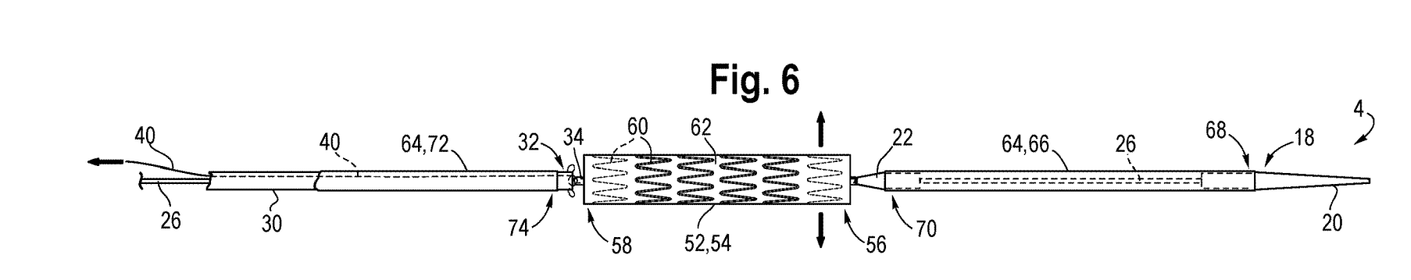
FIG. 6 illustrates the proximal end of the delivery device and the prosthesis fully deployed.

When the distal sheath segment 72 has been sufficiently retracted to expose the distal end 58 of the prosthesis, the user may then retract the distal trigger wires 40 and/or any other diameter reducing ties that may be present at the distal end 58 of the prosthesis (such as by manipulation of one or more trigger wire release mechanisms of the handle assembly 8) to allow the distal end 58 of the prosthesis to at least partially deploy radially outwardly within a vessel. At this point, the prosthesis 52 may be fully deployed within the vessel, as shown in FIG. 6. In another example, the handle assembly 8 may be manipulated further to facilitate release of other components, for example a top cap (not shown) necessary to allow the prosthesis 52 to fully deploy.

Figure 7:
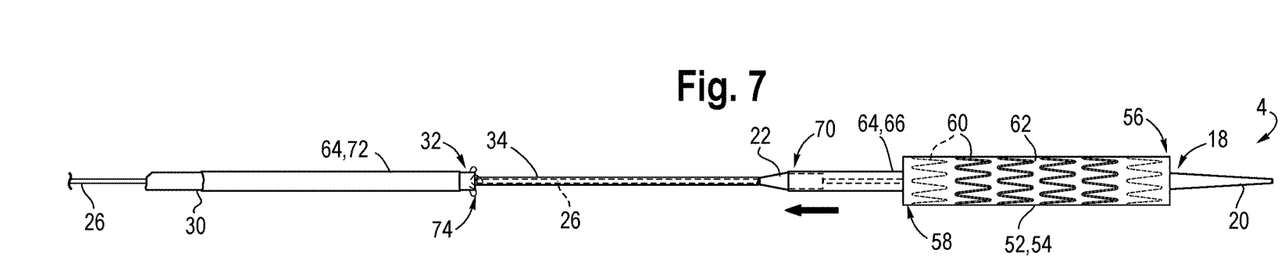
FIG. 7 illustrates the proximal end of the delivery device and the delivery device partially withdrawn after the prosthesis is fully deployed.
Figure 8:
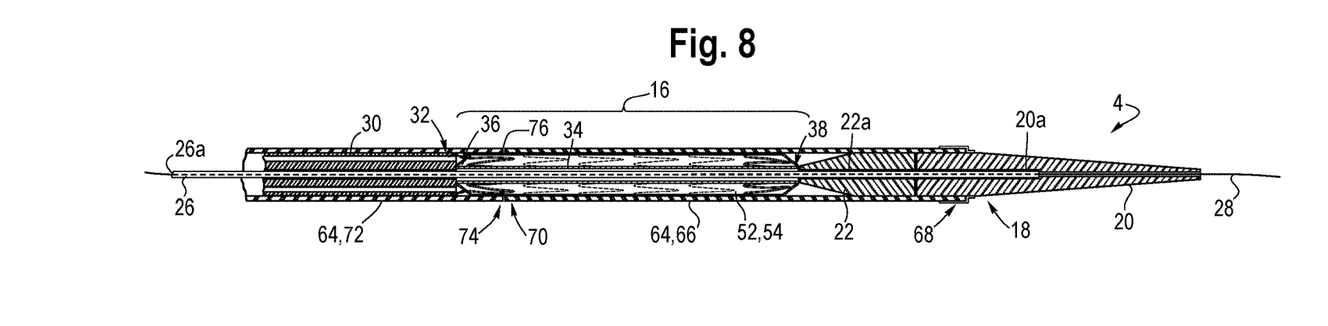
FIG. 8 is a cross-sectional side view of the proximal end of the delivery device and the prosthesis fully sheathed.

Once the prosthesis 52 has been fully released from the delivery device 2, the delivery device 2 can be removed from the patient's body. In one example, the delivery device 2 may be removed with the proximal sheath segment 66 and the segment 72 in the configuration described above when the prosthesis 52 is fully deployed, as shown in FIGS. 7 and 13. The reverse distal taper of the distal tip segment 22 may facilitate efficient and easy withdrawal of the delivery device 2 from the body with reduced risk of the tip assembly 18, the proximal sheath segment 66, or other portions of the delivery device 2 from snagging, catching or otherwise interfering with the deployed prosthesis 52. The delivery device 2 can then be withdrawn distally, through the lumen of the prosthesis and retracted further until the device has been safely removed from the patient's body.

Throughout this specification, unless the context requires otherwise, the words "comprise" and "include" and variations such as "comprising" and "including" will be understood to imply the inclusion of an item or group of items, but not the exclusion of any other item or group items. While various embodiments have been described, it will be apparent to those of ordinary skill in the art that many more examples and implementations are possible within the scope of the present disclosure. Furthermore, although various indications have been given as to the scope of this present disclosure, the present disclosure is not limited to any one of these but may reside in two or more of these combined together. Accordingly, the present disclosure is not to be restricted except in light of the attached claims and their equivalents.

The invention claimed is:

1. A system for the delivery and deployment of a prosthesis comprising:
a delivery device having a distal end and a proximal end, the delivery device comprising
an inner cannula extending between the distal end and the proximal end of the delivery device,
a positioner disposed coaxially over a first portion of the inner cannula,
a concentric cannula disposed coaxially over a second portion of the inner cannula, a distal end of the concentric cannula being attached to a proximal end of the positioner, and
a tip assembly disposed over a third portion of the inner cannula, the tip assembly comprising a distal tip segment and a separate proximal tip segment disposed proximally of the distal tip segment, the distal tip segment being attached to a proximal end of the concentric cannula, the proximal tip segment being attached to a proximal end of the inner cannula;

at least one trigger wire extending longitudinally within a lumen of the positioner and at least one suture loop attached to the proximal end of the positioner, a prosthesis carried on the concentric cannula at the proximal end of the delivery device; and a sheath mounted coaxially over the prosthesis, the sheath comprising a split defining a proximal sheath segment disposed proximally of the split and a distal sheath segment disposed distally of the split, a proximal end of the proximal sheath segment being attached to the proximal tip segment, wherein at least one end of the prosthesis is releasably coupled to the delivery device, and wherein a proximal end of the at least one trigger wire extends proximally beyond the proximal end of the positioner such that the at least one trigger wire passes through the at least one suture loop and is removably attached to a distal end of the prosthesis for releasably coupling the distal end of the prosthesis to the delivery device.

2. The system of claim 1, wherein the proximal tip segment has a forward proximal taper and the distal tip segment has a reverse distal taper.

3. The system of claim 1, wherein the inner cannula is moveably received within an inner lumen of the distal tip segment and is fixedly attached within an inner lumen of the proximal tip segment such that pushing the inner cannula in a proximal direction causes proximal movement of the proximal tip segment and the proximal sheath segment.

4. The system of claim 1, wherein a distal end the proximal sheath segment and a proximal end of the distal sheath segment are disposed over a portion of the prosthesis such that pushing the inner cannula in a proximal direction causes proximal movement of the proximal tip segment and the proximal sheath segment to expose the proximal end of the prosthesis and retracting the distal sheath segment distally to expose the distal end of the prosthesis.

5. The system of claim 1, wherein the proximal sheath segment is configured to be moveable proximally between a pre-deployment configuration in which a proximal end of the prosthesis is covered by the proximal sheath segment and a post-deployment configuration in which the proximal end of the prosthesis is uncovered by the proximal sheath segment and a distal end of the proximal sheath segment is disposed proximally the proximal end of the prosthesis and the distal sheath segment is configured to be moveable distally between a pre-deployment configuration in which a distal end of the prosthesis is covered by the distal sheath segment and a post-deployment configuration in which the distal end of the prosthesis is uncovered by the distal sheath segment and a proximal end of the distal sheath segment is disposed distally the distal end of the prosthesis.

6. The system of claim 1, wherein at least one end of the prosthesis is releasably coupled to the delivery device.

7. The system of claim 1, wherein the at least one trigger wire comprises three trigger wires and the at least one suture loop comprises three suture loops, the trigger wires being removably attached to the distal end of the prosthesis at radial positions approximately 120 degrees apart.

8. A method of deploying a prosthesis, the method comprising:

providing a delivery device including an inner cannula extending between a distal end and a proximal end of the delivery device, a positioner disposed coaxially over a first portion of the inner cannula, a concentric cannula disposed coaxially over a second portion of the inner cannula, a distal end of the concentric cannula being attached to a proximal end of the positioner, and a tip assembly disposed over a third portion of the inner cannula, the tip assembly having a distal tip segment and a separate proximal tip segment disposed proximally of the distal tip segment, the distal tip segment being attached to a proximal end of the concentric cannula, the proximal tip segment being attached to a proximal end of the inner cannula;

at least one trigger wire extending longitudinally within a lumen of the positioner and at least one suture loop attached to the proximal end of the positioner, wherein a proximal end of the at least one trigger wire extends proximally beyond the proximal end of the positioner such that the at least one trigger wire passes through the at least one suture loop and is removably attached to a distal end of the prosthesis for releasably coupling the distal end of the prosthesis to the delivery device;

providing a prosthesis, having proximal and distal ends, carried on the concentric cannula at the proximal end of the delivery device, wherein the proximal and distal ends of the prosthesis are releasably coupled to the delivery device;

providing a sheath mounted coaxially over the prosthesis, the sheath having a split defining a proximal sheath segment disposed proximally of the split and a distal sheath segment disposed distally of the split, a proximal end of the proximal sheath segment being attached to the proximal tip segment;

pushing the proximal sheath segment proximally simultaneously with the proximal tip segment so as to at least partially remove the proximal sheath segment from the prosthesis;

pushing the proximal sheath segment proximally so as to fully remove the proximal sheath segment from the prosthesis and expose a proximal end of the prosthesis;

retracting the distal sheath segment distally over the positioner to remove it from the prosthesis and expose a distal end of the prosthesis;

after pushing the proximal sheath segment proximally so as to fully remove the proximal sheath segment from the prosthesis and expose the proximal end of the prosthesis, uncoupling the proximal end of the prosthesis from the delivery device;

after retracting the distal sheath segment distally over the positioner to remove it from the prosthesis and expose the distal end of the prosthesis, uncoupling the distal end of the prosthesis from the delivery device; and uncoupling the distal end of the prosthesis from the delivery device includes retracting the at least one trigger wire at the distal end of the prosthesis.

9. The method of claim 8, wherein

The proximal tip segment has a forward proximal taper, the distal tip segment has a reverse distal taper, and the reverse distal taper is exposed when the proximal sheath segment is fully removed from the prosthesis.

10. The method of claim 8, wherein the proximal sheath segment is pushed proximally simultaneously with the proximal tip segment by pushing the inner cannula in a proximal direction.

11. The method of claim 8 wherein a distal end the proximal sheath segment and a proximal end of the distal sheath segment are disposed over a portion of the prosthesis.

12. The method of claim 8, wherein
the proximal sheath segment is configured to be moveable proximally between a pre-deployment configuration in which a proximal end of the prosthesis is covered by the proximal sheath segment and a post-deployment configuration in which the proximal end of the prosthesis is uncovered by the proximal sheath segment and a distal end of the proximal sheath segment is disposed proximally the proximal end of the prosthesis and
the distal sheath segment is configured to be moveable distally between a pre-deployment configuration in which a distal end of the prosthesis is covered by the distal sheath segment and a post-deployment configuration in which the distal end of the prosthesis is uncovered by the distal sheath segment and a proximal end of the distal sheath segment is disposed distally the distal end of the prosthesis.

13. The method of claim 8, wherein the at least one trigger wire comprises three trigger wires and the at least one suture loop comprises three suture loops, the trigger wires being removably attached to the distal end of the prosthesis at radial positions approximately 120 degrees apart.

\* \* \* \* \*